United States Patent [19]

Higerd et al.

[11] 4,268,434

[45] May 19, 1981

[54] IMMUNOSUPPRESSIVE EXTRACELLULAR PRODUCT FROM ORAL BACTERIA

[76] Inventors: Thomas B. Higerd, 922 Regatta Rd., Charleston, S.C. 29412; Jean-Michel C. Goust, 29 27th Ave., Isle of Palms, S.C. 29451

[21] Appl. No.: 2,234

[22] Filed: Jan. 9, 1979

[51] Int. Cl.³ .................... A61K 35/74; C12P 21/00
[52] U.S. Cl. .................... 260/112 R; 435/68; 435/826; 435/882
[58] Field of Search ............ 195/96; 435/68, 826, 435/882, 70, 71, 169, 170; 424/115, 177; 260/112 R

[56] References Cited

U.S. PATENT DOCUMENTS 4,150,116  4/1979  Taubman et al. ............... 424/88

OTHER PUBLICATIONS

Higerd et al., Infection and Immunity vol. 21, No. 2, pp. 567–574 (Aug. 1978).

*Primary Examiner*—Lionel M. Shapiro
*Attorney, Agent, or Firm*—George A. Loud

[57] ABSTRACT

Extracellular products of oral bacteria have been isolated and have been found to have immunosuppressive activity. Genus Streptococcus and genus Actinomyces are preferred, particularly *Streptococcus mutans*, *Streptococcus intermedius*, *Streptococcus salivarius*, *Actinomyces viscosus* and *Actinomyces naeslundii*.

17 Claims, 6 Drawing Figures

IMMUNOSUPPRESSIVE EXTRACELLULAR PRODUCT FROM ORAL BACTERIA

BACKGROUND OF THE INVENTION

The pathogenesis of dental disease of the soft tissue is poorly understood. Gingivitis, the clinical manifestation which follows the accumulation of bacterial plaque in the gingival crevice area, usually progresses to periodontal disease. It is reasonable to suppose that dental plaque contains a primary factor or factors contributing to initiation of periodontal disease.

A wide variety of microorganisms present in the debris from the human gingival crevice have been identified qualitatively and quantitatively, but only recently have investigations focused on the immune response of the host to plaque material. Considerable evidence has accumulated that plaque microorganisms and/or their products initiate periodontal inflamation by altering the immune response of the host.

It is generally thought that oral bacteria sensitize the host, i.e., can stimulate the proliferation of lymphocytes and that the products of sensitization result in destruction of bone and soft tissues of the peridontium. Accordingly, it is highly unexpected that bacterial products would inhibit an immune response.

The immune response in humans and most animals in either humoral, i.e., mediated by antibodies, or cellular, i.e., mediated by sensitized lymphocytes. In either case, the immune response and accompanying inflammation may have both protective and destructive effects on the host tissue. The humoral reaction in man and other animals is provided by antibodies, immunoglobulin materials produced by lymphocytes, which circulate in the blood and are capable of chemically combining with "foreign matter" to neutralize it. However, in certain cases, the presence of a specific antibody may be undesirable. For example, antibodies directed toward antigens on the surface of a transplanted, foreign organ will result in destruction of the organ by the host.

The precise role of antibody-mediated immunity in the pathogenesis of periodontal disease is obscure, but serum antibodies against oral bacteria have been detected in patients with periodontal disease and the importance of cell-mediated immunity in periodontal disease has been suggested. The presence of bacterial factors capable of transforming lymphocytes and, presumably, enhancing antibody production, have been reported and these bacterial factors have been demonstrated in sonicates, extracts, and heated culture fluids from oral bacteria as well as sonicates or extracts of dental plaque and saliva. See generally, T. B. Higerd, et al "Inhibitory Effects of Extracellular Products from Oral Bacteria on Human Fibroblasts and Stimulated Lymphocytes", Infection and Immunity, August, 1978, pp. 567–574, and the references cited therein, which are herein incorporated by reference.

Extracellular products of oral bacteria may be involved in the pathogenesis of periodontal disease, since the lesion is found distant from the dental plaque. These products might also interfere with the function of fibroblasts, since early loss of collagen in periodontal disease may be directly related to the ability of fibroblasts to produce or catabolize collagen. It has been found that extracellular products from cultured oral bacteria, in accordance with the instant invention, are capable of inhibiting both proliferation of human fibroblastoid cell lines and blast transformation of stimulated human peripheral lymphocytes from normal individuals. Therefore, such products may be implicated in the pathology of periodontal disease and/or may interfere with the immune defense of the host against invading microorganisms.

Immunosuppressive materials have been obtained from blood extracts, e.g., immunoglobin derived from human blood lymphocytes by Thomas et al (U.S. Pat. No. 4,009,257) and gamma-globulins isolated by Bonneau et al (U.S. Pat. No. 4,056,614). γ-Linoleic acid is reported by Williams (U.S. Pat. No. 3,993,775) to have an immunosuppressive effect. Histaminase, an enzyme, in combination with an anti-microbial material, is said to substantially reduce reactions of the reticuloendothelial system (Van Leeuwen, U.S. Pat. No. 3,721,733).

It will be appreciated that, because suppression of a normal immune response may be highly desirable in certain clinical contexts, there is a need for additional sources and kinds of effective, non-toxic immunosuppressant materials.

SUMMARY OF THE INVENTION

In one aspect, this invention relates to extracellular immunosuppressive bacterial products from oral bacterial organisms. Preferred sources are members of genus Streptococcus and genus Actinomyces, particularly, *Streptococcus mutans*, *Streptococcus intermedius*, *Streptococcus salivarius*, *Actinomyces viscosus* and *Actinomyces naeslundii*.

In a preparative aspect, this invention relates to a method of producing an extracellular immunosuppressive bacterial material from an oral bacterial organism, comprising the steps of:

(a) culturing the oral bacterium anaerobically in a culture medium, (b) separating the oral bacterium from the culture medium to produce a bacteria-free protein-containing liquid, and (c) fractionating and concentrating the liquid from (b).

The thus-isolated immunosuppressive products of the present invention are of interest particularly with respect to having the capability of suppressing the immune system of a host. The materials, therefore, can be used in health care delivery for suppressing the natural immunity in patients receiving organ or tissue transplants, in patients suffering from "autoimmune diseases" and in patients hypersensitized to a variety of antigens.

Additionally, the extracellular product of *S. intermedius* has shown effectiveness in the treatment of tumors in laboratory test animals, indicating the possibility of broader utility in the treatment of other mammals.

DESCRIPTION OF PREFERRED EMBODIMENTS

The immunosuppressive agents of the present invention are protein fractions of extracellular products of oral bacteria. The oral bacteria which are sources of the proteinaceous immunosuppressive agents of the present invention include members of genus Streptococcus and genus Actinomyces, e.g., *Streptococcus mutans, Streptococcus intermedius, Streptococcus salivarius, Actinomyces viscosus* and *Actinomyces naeslundii.* All of these agents have molecular weights in the range of 10,000 to 1,000,000, as measured by gel filtration on "Sephadex G-200" and "Ultragel Ac A 34". The proteinaceous products have a particle size not greater than 0.22 microns in view of the fact a 0.22 micron millipore filter may be used for sterilization, a protein content between 50 and 100% (most nonproteins are smaller molecular weight), a lipid content below 20% (one needs to use polar solvents on whole cells to remove a significant amount of lipid), and a carbohydrate content below 30% (by assay, about 4% was carbohydrate). The percentage values being dry weight per volume exclusive of the salts contained in the buffer which is PBS (0.05 M phosphate buffer, pH about 7.2, with 0.15 M NaCl (about 0.85%)). 10 mg of the product presents a transparent solution which may have a brown coloration when present in one milliliter of PBS. The agents can be made sterile and isotonic.

A. Mode of Preparation

The selected bacteria may be grown on the upper surface of microporous membranes, the pore size of which is selected to allow nutrients to pass through the membrane from the nutrient agar below to the microorganisms above to permit growth. At the same time, the membrane blocks the passage of larger bacterial products from the microorganism side so that the products remain close to the bacteria and do not diffuse into the medium below.

Following incubation, the membrane to the upper surface of which are affixed the bacteria and their products, is removed from the nutrient surface and washed with phosphate buffer so that the wash contains the bacteria and the product. The bacteria are removed from the wash by centrifugation and the supernatant is characterized.

Figure 1:
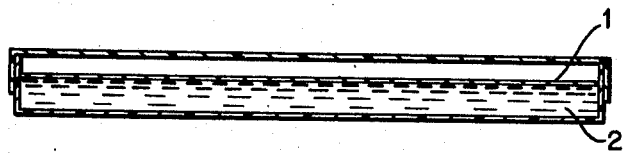
In FIG. 1 is shown an apparatus in which the bacterial products can be prepared.

In FIG. 1 is shown a Petri dish filled with a nutrient medium (1), atop of which is placed a microporous membrane (2).

Other methods known in the art for obtaining extracellular products of bacterial/mycotic origin can be used, e.g., as discussed by Prescott and Dunn, *Industrial Microbiology*, 3rd edition, McGraw-Hill Co., New York, N.Y.

The above-mentioned cultivation method using a membrane is valuable for experimental purposes, but it will be understood that preparation of a broth culture and isolation of extracellular immunosuppressive materials therefrom is preferred for commercial exploitation of this invention.

A preferred medium for culturing the oral bacteria is tryptone-glucose-agar (TGA), which contains 15-25 g. of tryptone, 2-8 g. of glucose, 3-5 g. of $K_2HPO_4$, 0.5-1.5 g. of $KH_2PO_4$, NaCl, $MgSO_4$, and $MnSO_4$ per liter of water. More preferably the medium contains 20 g. of tryptone, 5 g. of glucose, 4 g. of $K_2HPO_4$, 2 g. of NaCl, 250 mg. of $MgSO_4.7H_2O$, 17 mg. of $MnSO_4$ and 15 g. of agar per liter of distilled water.

Other media can be used, e.g., Todd-Hewitt broth, trypticase soy agar, salivarius-mitis broth, meat infusion agar, cooked meat broth, etc.

The organisms may be incubated for 12-96 hours at 35°-40° C. Preferably, the incubation is carried out at 37° C. for 24-48 hours.

B. ISOLATION

After cultivation the bacterial cells are preferably separated (from the culture medium) by centrifugation, but any conventional form of solids separation, including various modes of filtration, may be employed. Likewise, while the preferred mode of fractionation/concentration is ultrafiltration, other conventional means of isolating the desired protein fraction may be employed. For example, molecular sieving, evaporation, ion exchange, gel filtration or any combination thereof may be used for fractionation. Salting out (or fractional precipitation), e.g., with ethanol, acetone or ammonium sulfate, is another conventional fractionation technique which may be employed alone or in combination with any of the foregoing.

C. Inhibitory Activity

The extracellular products were tested for their ability to inhibit $^3H$-thymidine uptake by established human fibroblastoid cell lines. The products were diluted at least 1:40 in Eagle's minimum essential medium (MEM) to prevent pH or salt effects from interfering with the assay and all samples were diluted so that 2 µg. protein was added to each well. The results were regarded as insignificant when inhibition was below 15%. Four strains of *S. mutans*—AHT, BHT, 10449, and IB—produce factors which significantly inhibit fibroblast proliferation as measured by $^3H$-thymidine uptake. In no instance did products from all strains belonging to a given serotype cause inhibition. The bacterium isolated from human dental plaque and classified by the Communicable Disease Center (Atlanta, Ga.) as *S. intermedius* consistently gave the highest percent inhibition. *A. viscosus*, but not *A. naeslundii*, produced substances that inhibited proliferation of fibroblasts.

Using PHA-stimulated lymphocytes as targets, aliquots of the same preparations as used in the experiments with fibroblasts were added to microtiter wells containing mononuclear cells, and the percent inhibition of $^3H$-thymidine incorporation following blast transformation was calculated. Preparations from *S. mutans* strains AHT, E49, BHT, and Fa-1 caused significant inhibition. *S. intermedius* products were particularly effective, with a correlation coefficient for linear regression of 0.988. For example, 210 ng. of the *S. intermedius* product gave 25% inhibition, and approximately 2 µg. was calculated to give complete inhibition of $^3H$-thymidine uptake by PHA-stimulated lymphocytes. *A. naeslundii, A. viscosus* and *S. salivarius* were able to inhibit thymidine uptake. *S. mutans* E49, *S. salivarius*, and *A. naeslundii* appear to elaborate substances which inhibit blast transformation or peripheral lymphocytes but lack the ability to inhibit fibroblasts.

Partial purification of the inhibitory factor or factors was achieved by passage of an aliquot of a crude preparation, for example, from *S. intermedius* through a Sephadex G-200 column. The resulting chromatographic profile revealed a single peak of biological activity when the fractions were assayed for the capacity to inhibit $^3$-H-thymidine incorporation by fibroblasts of PHA-stimulated lymphocytes. The molecular weight of this fraction was estimated as approximately 160,000 by comparison with the elution profiles of proteins of known molecular weight. Gel filtration of the crude preparation of Ultragel AcA34 gave a similar estimated molecular weight of the biologically active material. Purity of a typical crude preparation from *S. intermedius* and concentrated fractions from Sephadex G-200 having biological activity were subjected to slab SDS-polyacrylamide gel electrophoresis. The resulting protein pattern showed the presence of about 40 proteins in the crude preparation and about 25 proteins in the G-200 biologically active fraction.

The apparent absence of 260 nm-absorbing material in preparations from *S. intermedius* obtained by the dialysis membrane technique suggests that inhibition in accordance with the invention is not caused by intracellular metabolites resulting from bacteriolysis. The well-defined elution pattern from gel filtration chromatography suggests that the inhibitor from this organism probably is not capsular or endotoxin material. The inhibitory factors are considered "microbial products" because of lack of evidence of microbial lysis, because control preparations harvested under identical conditions but lacking microorganisms lacked biological activity, and because a well-defined population of proteins was demonstrated. Failure of attempts to obtain biologically active material by procedures involving cell disruption, e.g., freeze-thaw, sonication and passage through the French pressure cell, also strongly suggest that the product is extracellular rather than intracellular.

The ability of extracellular products from oral bacteria to inhibit blast transformation of PHA-stimulated lymphocytes suggests that microorganisms within the oral cavity are capable of modifying the host's immune response.

In one aspect, the preferred product of this invention inhibits fibroblastoid cells and is obtained from *S. mutans* AHT, BHT, 10449 or IB; *S. intermedius* or *A. viscosus*. In another preferred aspect, the products of this invention inhibit blast transformation of PHA-stimulated human lymphocytes and are obtained from *S. mutans* AHT, BHT, Fa-1 or E49; *S. intermedius, A. viscosus* or *A. naeslundii*.

More preferably, the product exhibits both types of inhibitory activity and is isolated from *S. mutans* AHT, *S. mutans* BHT, *S. intermedius* or *A. viscosus*. Most preferably, the extract is isolated from *S. intermedius* and the molecular weight of the immunosuppressive factor is about 160,000 and the pI is 4.8.

In one preferred preparative aspect, the culture medium is broth.

When a solid medium containing agar is used, the preferred culture medium is tryptone-glucose-agar and the oral bacterial organism is

*Actinomyces naeslundii,*
*Actinomyces viscosus,*
*Streptococcus mutans* AHT,
*Streptococcus mutans* E49,
*Streptococcus mutans* (ATCC 10449),
*Streptococcus mutans* BHT,
*Streptococcus mutans* Fa-1,
*Streptococcus mutans* IB,
*Streptococcus intermedius,* or
*Streptococcus salivarius.*

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE I

Preparation of Extracellular Products (a) Organisms and Media

Actinomyces sp. were furnished by Dr. John K. Dyer, Department of Oral Biology, University of Nebraska, and *Streptococcus sanguis* 10556 was obtained from the American Type Culture Collection (ATCC). All other strains were the gift of Dr. Robert H. Staat, Department of Oral Biology, University of Louisville. The microorganisms were grown anaerobically at 37° C. for 24 hours in tryptone-glucose-agar (TGA) consisting of 20 g. of tryptone, 5 g. of glucose, 4 g. of $K_2HPO_4$, 1 g. of $KH_2PO_4$, 2 g. of NaCl, 250 mg. of $MgSO_4.7H_2O$, 17 mg. of $MnSO_4$, and 15 g. of agar dissolved in 1 liter of distilled water.

(b.1) Plate Culture and Isolation of Extracellular Products

Discs of sterile dialysis membranes (12,000 to 14,000 molecular weight cutoff) of the same diameter as Petri dishes (100 mm.) were placed on the agar surface of fresh plates. An aliquot (0.1 ml) of a bacterial cell suspension ($1 \times 10^8$ cells/ml.) was spread over the dialysis membrane with a cotton swab. The plates were incubated at 37° C. under anaerobic conditions. After 48 hours of incubation, the dialysis membranes were removed and washed with a minimal volume of 0.05 M potassium phosphate buffer (pH 7.5). The wash was clarified by centrifugation at 29,000×g for 15 min. and the supernatant concentrated about 10 fold by positive pressure ultrafiltration using an Amicon PN-10 filter. The final solution, designated "extracellular products" was analyzed for protein concentration of the retentate by a nomograph of $^A$280 nm. and $^A$260 nm. based on extinction coefficients for enolase and nucleic acid as as reported by Warburg and Christian, Biochem Z. 310:384, 1942.

Since concentrated washes of sterile discs harvested from uninoculated TGA medium had neither detectable protein bands following electrophoresis nor biological activity, contamination from the medium was considered negligible. No attempt was made to solubilize proteins that were bound to cells or cellular debris.

For *S. intermedius*, submitted to ATCC on May 17, 1978, and now numbered ATCC-31412 the concentration was typically 4–11 mg. protein/ml.

In the case of other organisms, the retentates contained:

| Organism | Incubation period | (mg. protein/ml.) Retentate* |
|---|---|---|
| *S. mutans* AHT | 48 hours | 3.7 |
| *S. mutans* OMZ 61 | " | 2.0 |
| *S. mutans* E49 | " | 1.6 |
| *S. mutans* BHT | " | 2.2 |
| *S. mutans* Fa-1 | " | 2.7 |

-continued

| Organism | Incubation period | (mg. protein/ml.) Retentate* |
|---|---|---|
| S. mutans 10449 | " | 1.6 |
| S. mutans GS-5 | " | 2.1 |
| S. mutans IB | " | 1.5 |
| S. mutans SL-1 | " | 0.8 |
| S. mutans OMZ 176 | " | 1.6 |
| S. mutans LM7 | " | 1.7 |
| S. mutans B2 | " | 1.1 |
| S. intermedius-MG | " | 8.0 |
| S. salivarius | " | 2.2 |
| S. sanguis 10556 | " | 1.6 |
| A. naeslundii | " | 2.2 |
| A. viscosus | " | 2.2 |

*All samples were diluted with MEM prior to assay in order to obtain a uniform 100 µg of protein/m. for each test solution.

(b.2) Broth Culture

While any medium that will support growth may be used, Todd-Hewitt broth gave the best experimental results and is preferred. Todd-Hewitt broth is passed through a hollow fiber dialysis unit with a molecular cut-off of 50,000. The filtrate is sterilized and used as the liquid medium which is inoculated with *Streptococcus intermedius*. After 48 hours at 37° C., the culture is harvested and centrifuged to remove the bacteria. The supernatant is then passed through the same hollow fiber apparatus for concentration and the retentate is saved.

The crude product (retentate) is next applied to an anion exchange liquid chromatography column, DEAE-Sephacel. After rinsing to remove or wash-out any material not adhering, a salt (NaCl) linear gradient from 0.0 M to 1.0 M is applied. At approximately 0.3 M NaCl, a 280 nm peak absorbance material is eluted which contains the biological activity.

(c) Determination of Extent of Cell Lysis

Figure 2:
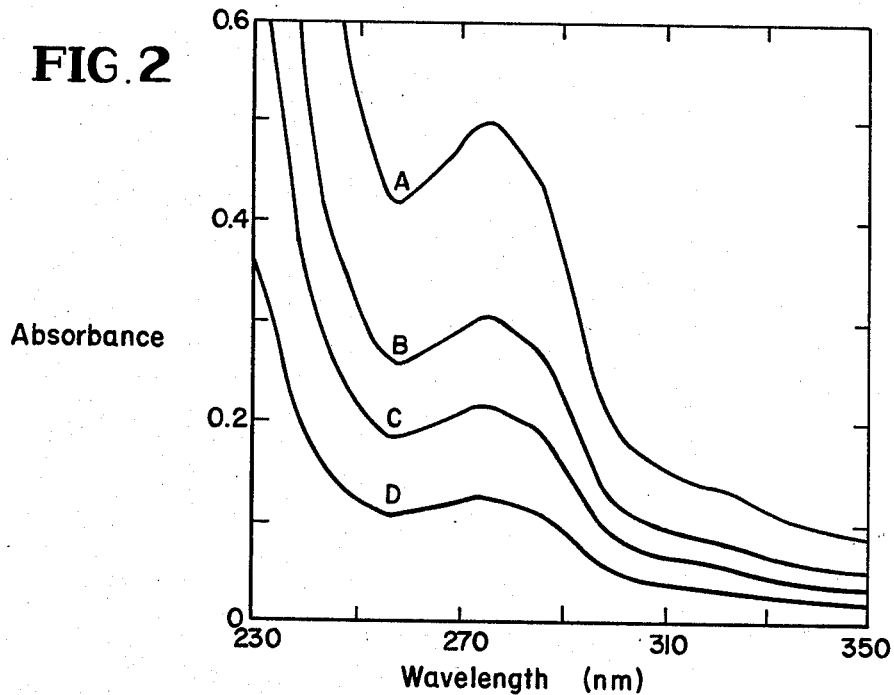
FIG. 2 is an ultraviolet absorptivity profile of a dialyzed preparation of *S. intermedius*.

Ultraviolet absorption profiles of *S. intermedius* preparations after exhaustive dialysis against distilled water were determined. As shown in FIG. 2, a single peak of absorbance occurred at 275 nm., with minimal absorbance at 256 nm. These spectral characteristics indicate insignificant nucleic acid contamination and therefore negligible cell lysis. Morphological examination by light microscopy revealed >95% of the cells intact. In addition, since activity could not be recovered from broken cells, it appears that the biological activity is of extracellular origin.

EXAMPLE II

Activity of Extracellular Products (a) Assay of Fibroblast Inhibitory Factor

HeLa (established from human carcinoma of the cervix) and AV3 established from human anmion) cell lines were grown in monolayer culture. At confluency, 0.25% trypsin-EDTA (Gibco, Grand Islands, N.Y.) in sterile PBS was added to the culture flask. After detachment, the cells were centrifuged, washed twice in Eagle's minimal essential medium (MEM) and resuspended in MEM with 10% fetal calf serum at a final concentration of 1×10⁴ cells/ml.

Each well of a Falcon Microtiter plate was seeded with 100 µl. of the suspension (10³ cells), followed by incubation for 2-4 hours at 37° C. to allow the cells to attach. Then 100 µl. of the bacterial product being tested, using twofold serial dilutions with MEM containing 20% fetal calf serum, was added to each well. The plates were incubated for 5 days at 37° C. in an air-CO₂ (95%:5%) incubator and pulsed with 0.2 µCi of ³H-thymidine (Sp. Act. 1.9 Ci/mmol; New England Nuclear Corp., Boston, Mass.) for the last 18 hours. The supernatants were removed and 0.2 ml. of 0.25% trypsin-EDTA in sterile PBS was added to each well. After complete detachment from the bottom of the wells, the cells were harvested onto glass fiber strips using a Multiple Automated Sample Harvester (Mass II; Microbiological Associates, Bethesda, Md.), dried, and transferred to vials containing 2 ml. of Omnifluor before counting in a beta scintillation counter (Packard Tricarb #3380). The formula used to calculate percent inhibition was $$\%I = 100 \times \frac{cpm \text{ experiment}}{cpm \text{ control}} - 100$$

Results in the presence of 2 µg. of protein per well are given in Table I.

(b) Assay for Inhibition of Blast Transformation

Heparinized peripheral blood from healthy volunteer blood donors was diluted 1:3 with Hanks Balanced Salt Solution (HBSS) and centrifuged for 35 minutes at 400×g upon Ficoll Isopague gradients. The mononuclear cell layer was harvested, washed 3 times with HBSS and resuspended at a final concentration of 2×10⁶ cells/ml. in minimal essential medium (MEM) augmented with 10% fetal calf serum. 100 µl. of the cell suspension was added to each well of a Falcon Microtiter Plate. Controls with and without phytohemagulutinen, a well known lectin (Grand Island Biological Co.; PHA) were placed in cultures simultaneously with test cells, which were stimulated with PHA at a level of 1.2+0.12 µl. of the original solution per well. The bacterial products being tested were added in twofold serial dilutions (in MEM with 10% fetal calf serum) to a final volume of 0.2 ml. The cells were incubated at 37° C. for 2 days before pulsing overnight with ³H-thymidine as described above. The lymphocytes were collected with the automatic harvester onto glass fiber strips and dried. The radioactivity was determined in a Packard beta scintillation counter.

The formula used to calculate percent inhibition of lymphocyte blast transformation was $$\%I = 100 \times \frac{cpm \text{ experiment} - cpm \text{ unstimulated}}{cpm \text{ stimulated with PHA alone} - cpm \text{ unstimulated controls}} - 100$$

Results of assays in the presence of 2 µg. of protein per well are given in Table I.

Figure 3:
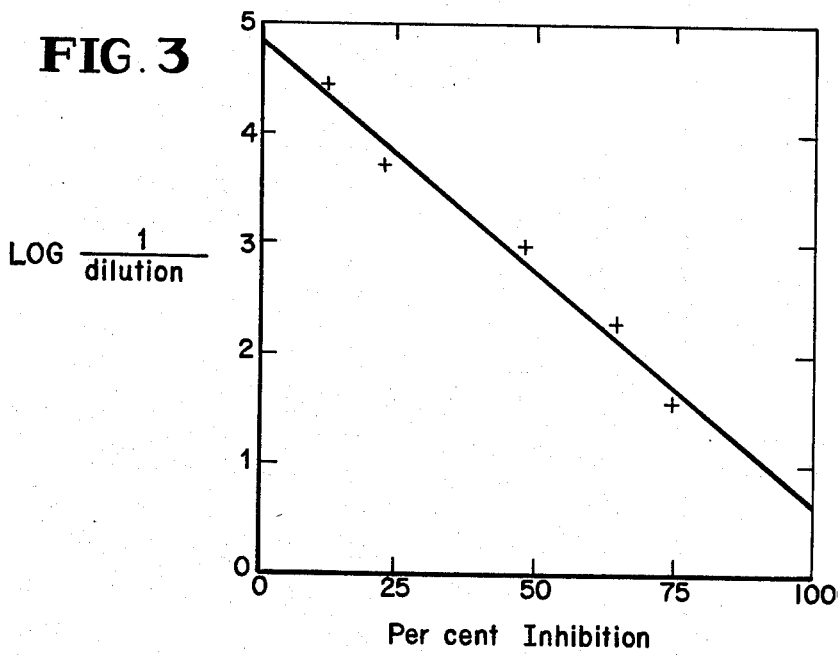
FIG. 3 shows the inhibitory activity of a preparation from *S. intermedius* (100 μg. of protein/ml.), assayed in cultures of PHA-stimulated human lymphocytes.

In FIG. 3 is given a representative plot of inhibitory activity of extracellular products from a crude preparation of *S. intermedius*, containing 100 µg. of protein/ml., assayed in cultures of PHA-stimulated peripheral human blood lymphocytes.

TABLE I

Inhibition of a 3$_H$-thymidine uptake by fibroblasts and PHA-stimulated lymphocytes in the presence of extracellular products from various oral bacteria

| Bacterial Strain | Serotype (Brathall. 1970. Odont. Rev. 21:143-152) | Inhibition (%) | |
|---|---|---|---|
| | | Fibroblasts (AV3) | PHA-stimulated lymphocytes |
| S. mutans AHT | a | 24 | 22 |

TABLE I-continued

Inhibition of a $^3H$-thymidine uptake by fibroblasts and PHA-stimulated lymphocytes in the presence of extracellular products from various oral bacteria

| Bacterial Strain | Serotype (Brathall. 1970. Odont. Rev. 21:143-152) | Inhibition (%) Fibroblasts (AV3) | PHA-stimulated lymphocytes |
|---|---|---|---|
| S. mutans OMZ 61 | a | —* | —* |
| S. mutans E49 | a | —* | 42 |
| S. mutans BHT | b | 72 | 45 |
| S. mutans Fa-1 | b | —* | 16 |
| S. mutans 10449 | c | 17 | —* |
| S. mutans GS5 | c | —* | —* |
| S. mutans IB | c | 22 | —* |
| S. mutans SL1 | d | —* | —* |
| S. mutans OMZ 176 | d | —* | —* |
| S. mutans LM7 | e | —* | —* |
| S. intermedius | — | 84 | 85 |
| S. salivarius | — | —* | 38 |
| S. sanguis 10556 | — | —* | —* |
| A. naeslundii | — | —* | 69 |
| A. viscosus | — | 19 | 32 |

*not significant (inhibition less than 15%)

The inhibitory effect is reproducible and is observed even if the extracellular bacterial product is added to the cell culture just before pulsing with $^3H$-thymidine. The inhibitory effect is thought not to be due to cytotoxicity, because more than 90% of the cell culture is viable at the end of the three-day testing cycle. Fresh human lymphocytes that have been preincubated with the extracellular bacterial product from S. intermedius can be washed and their ability to be stimulated by a mitogen or an antigen remains unhampered.

Similar results are obtained using other mitogenic lectins as erythrocyte stimulants, e.g., concanavalin A and pokeweed mitogen, over a three-day test cycle or an antigen, e.g., tuberculin PPD, over a five day cycle.

(c) Cytofluorographic Analysis

Lymphocytes were cultured as above for three days, with or without a mitogen or dilution of the extracellular product resuspended in calcium magnesium-free citrate buffered saline with EDTA and triton X100, and strained with acridine orange ($10^{-5}$ M). Histograms of green (DNA) stained cells were recorded and the percentage of cells in $G_1$, S, $G_2$ and M were recorded; and histograms of red (RNA) stained cells were obtained, wherein $G_1$ corresponds to resting, nonproliferating cells
S defines cells whose DNA content is increasing up to the $G_2$ phase
$G_2$ is the phase of growth when the DNA content is twice the amount found in the $G_1$ phase
M is for the mitotic phase (and cannot be differentiated from $G_2$ by the method used).

The results suggest that both DNA and RNA synthesis of stimulated lymphocytes are blocked in vitro.

(d) Testing Human Lymphoblastoid Cell Lines

The extracellular material from S. intermedius inhibits the following lines: RPMI 1788, PGLC 33H, SWB-16 (B cell lines and CCRF-CEM (T cell line) as determined by a testing sequence in which lymphoid cell lines were grown in MEM supplemented with 10% fetal calf serum at a cell concentration ranging from $5\times10^5$ to $5\times10^6$ cells/ml. After harvesting, the cells were adjusted to a concentration of $2\times10^6$/ml. in MEM supplemented with 10% fetal calf serum. A 0.1 ml. aliquot ($2\times10^5$ cells) was added to individual wells of microtiter plates. To the cells, twofold serial dilutions of the extracellular product being tested was added so that the final volume was 0.2 ml. Each dilution was tested in triplicate. Also, three wells were supplemented with 0.1 ml. of MEM containing 10% fetal calf serum to serve as controls.

The microtiter plate was incubated overnight at 37° C. in a humidified incubator, pulsed with $^3H$-thymidine (0.2 µCi/well), incubated for four to eight hours and harvested with the multiple automated sample harvester. $^3H$-thymidine uptake was determined by counting radioactivity in a Packard β Scintillation Counter and the percentage of inhibition determined as described above.

Flow cytofluorometry employing a 4802 cytofluorograph (Ortho Instruments) was used to determine the DNA content of the same cell lines after incubation with the same preparation of bacterial extracellular products. In addition, the percentage of cells in $G_1$, S and $G_2$-M phases of the mitotic cycle was also determined by this method. The percentage of viable cells was determined by the trypan blue exclusion test.

Results are given in Table II for the lymphoid cell lines, PGLC-33H, SWB 16, and CCRF-CEM. $^3H$-Tymidine uptake is inhibited in a dose responsive manner, although to different extents. The most sensitive cell line is PGLC-33H and the least sensitive CCRF-CEM. This is not due to a cytotoxic effect, because dilutions which inhibit $^3H$-thymidine uptake by more than 90% are not accompanied with a decrease in viability.

TABLE II

| | | Control | S 1/640 | S 1/320 | S 1/160 |
|---|---|---|---|---|---|
| $G_1$ | RPMI-1788 | 68.9% | 68.0% | 70.3% | 75.9% |
| | PGLC-33H | 64.9% | 72.0% | 81.7% | 77.9% |
| S-$G_2$M | RPMI-1788 | 31.1% | 26.0% | 23.5% | 19.8% |
| | PGLC-33H | 24.9% | 17.3% | 12.3% | 9.8% |

Extracellular bacterial products from S. intermedius(s) neither inhibit DNA synthesis nor decrease the percentage of cells in the S, $G_2$—M stage of the cell cycle in the lymphoid cell lines RPMI-1788 and PGLC-33H as shown in Table II.

Therefore, extracellular products inhibit lymphoid cell lines from proliferating but have no cytotoxic effect.

(e) Anti-tumor activity

The tumor tested is designated t1699 and is a spontaneous tumor in a particular strain of mice (DBA). From an animal with this spontaneous tumor, Haskill et al managed to culture the tumor and can maintain the cell line in permanent culture. When cultured cells are injected into female DBA mice in the stomach area, a certain percentage of animals will develop a hard tumor that will spontaneously disappear. However, when the cultured cells are injected in the shoulder pad, a tumor will develop, increase in size and eventually (about 60 days) kill the host. No instance has been found where spontaneous regression of the tumor exists when the animal is injected in the shoulder pad.

To test the agents of the present invention, $10^5$ tumor cells (1969) were injected into the shoulder of DBA mice at day 0. After 7 days, palpable tumor existed at the site of injection. The tumors were measured (mean diameter from two planes) and grouped into 4 groups of 10 animals each. Each group was compiled such that there was an even distribution of tumor size among the 4 groups. Group 1 received no treatment, Group 2 received a known anticancer drug, melphelan, Groups 3 and 4 received I.P. injections of the agent, produced from *Streptococcus intermedius* in example I (b)2, twice daily for 3 weeks beginning on day 7 and 14, respectively. The results were as follows:

Group 1: tumor size continued to increase and eventually killed the animals;

Group 2: 4 of the 10 animals showed no increase in tumor size for approximately 1½ weeks but soon tumor size continued to increase parallel to the control (Group 1). The other 6 animals were without effect in that their tumor size increased with the control group;

Group 3: all the mice showed progression of the tumor size insignificant from the control group;

Group 4: 3 out of the 10 mice had immediate regression in tumor size from about 6 mm to less than 1 mm. 1 of the three after two weeks, however, began an increase in tumor size. The other 2 that regressed, had complete regression of their tumor and, after 3 months, there was no evidence of a tumor growth. The other 7 animals in the group had progressive tumors that were indistinguishable from the control group. Thus, there appears to be anti-tumor activity in our preparation when assayed in the mouse mammary adenocarcinoma model if the treatment is initiated 14 days after the tumor implant.

EXAMPLE III

Characterization of the Inhibitory Factor (a) Column Chromatography and gel Filtration Preparations of *S. intermedius*-MG (ATCC-31412) and *A. naeslundii* (ATCC-12164) were dialyzed against phosphate-buffered saline (PBS) overnight and applied to a chromatographic column of (a) Sephadex G-200 (Pharma Fine Chemicals, Piscataway, N.J.) equilibrated with the same buffer (0.15 cm×60 cm., 2-ml. fractions collected) or (b) LKB Ultragel AcA34 (LKB Produkter AB, Bromma, Sweden) equilibrated with the same buffer (0.25 cm×91 cm, 8.4-ml. fractions collected).

Figure 4:
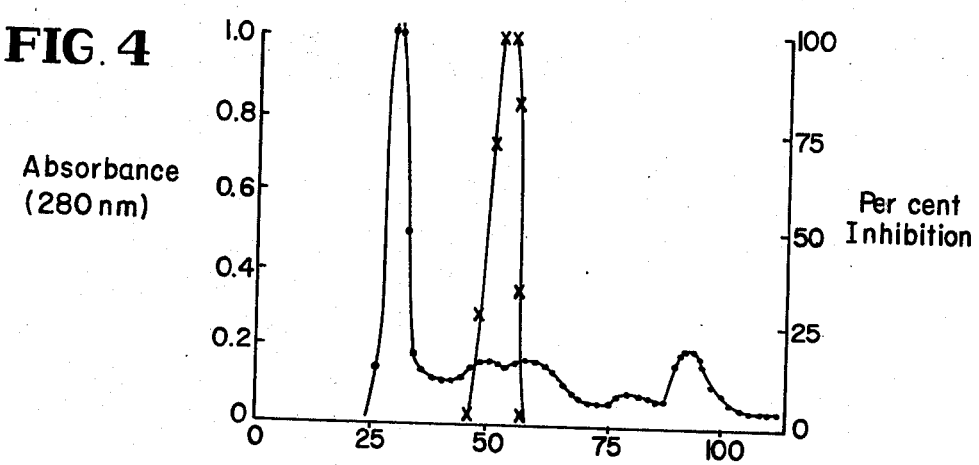
FIGS. 4 and 5 show fractionation of inhibitory activity of a preparation from *S. intermedius* on Sephadex G-200 and Ultagel Ac A 34, respectively.
Figure 5:
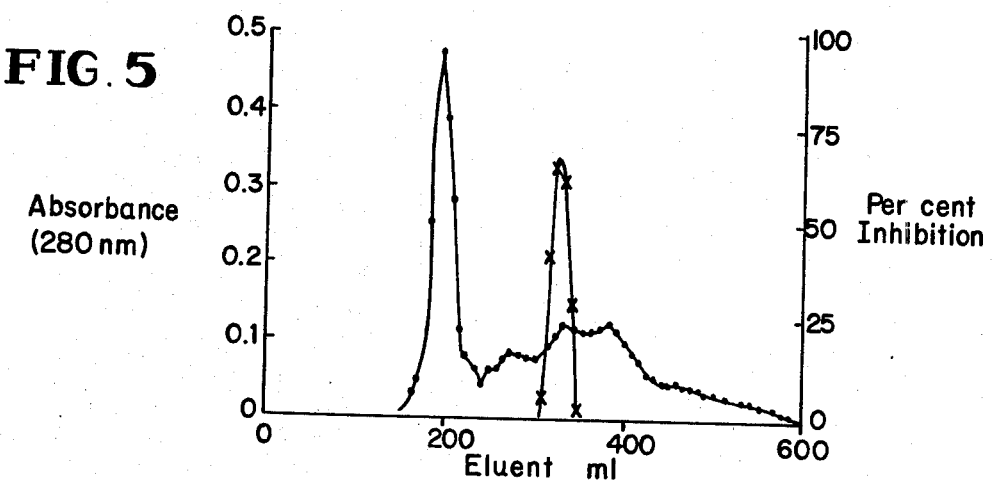

Changing absorbancy at 280 nm was followed as denoted by the line _____ in FIGS. 4 and 5 for Sephadex G-200 and Ultragel AcA34, respectively for a crude preparation from *S. intermedius*. An aliquot of each fraction was diluted 1:10 in MEM, sterilized by Millipore filtration, and assayed for inhibitory capacity against PHA-stimulated lymphocyte as described in Example II (b). Results are designated by the line X—X—X in FIGS. 4 and 5. From comparison with elution profiles of proteins of known molecular weights, the active fraction is thought to have a molecular weight of about 160,000.

When AV3 fibroblasts were used as target cells, the peak of inhibitory activity obtained from both chromatographic columns was indistinguishable from the profile for the activity assayed against stimulated lymphocytes.

(b) Gel Electrophoresis

Thin-layer sodium dodecyl sulfate-polyacrylamide gel electrophoresis was carried out by the procedure described by Karam and Bowles, *J. Virology*, 13:428–438, 1974, and the gel was stained with a 0.02% Coomassie Brilliant Blue solution.

The crude material contained about 40 fractions, whereas the purified protein contained about 25.

EXAMPLE IV

Thermal Stability of Extracellular Extracts

Figure 6:
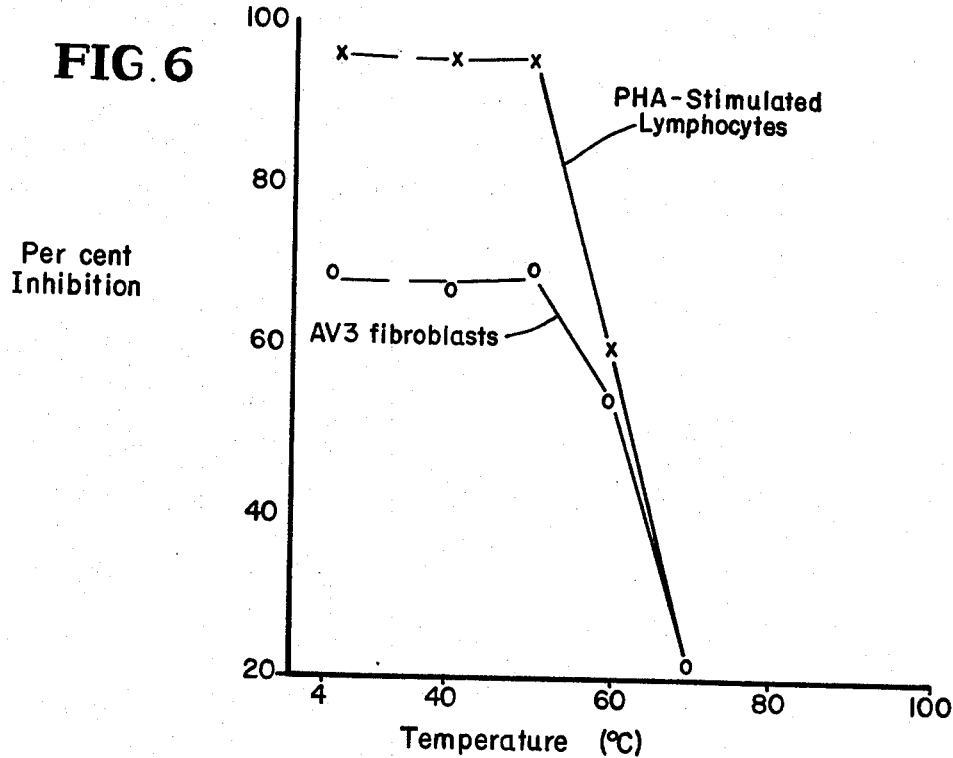
FIG. 6 shows the effect of heat on the biological activity of *S. intermedius* crude preparations.

Aliquots of the crude preparation from *S. intermedius* (Example I(b)1) were kept at various temperatures for 10 min. All samples were cooled in an ice bath to about 4° C., diluted appropriately, and assayed for residual biological activity. As shown in FIG. 6, the inhibitory activities for fibroblasts and for PHA-stimulated lymphocytes activity were retained after heating at 50° C. for 10 min., but lost after heating at temperatures above 70° C. These results suggest that the heat-labile active material is a protein.

EXAMPLE V

Effect on Rosette Formation

Preparations of the product of Example I(b)1 did not modify rosette formation between lymphocytes and sheep red blood cells at a concentration giving 100% inhibition of $^3$H-thymidine uptake in vitro.

EXAMPLE VI (a) In vivo Toxicity Testing

The extracellular bacterial products prepared in Example I(b)1 from *S. intermedius* (4 mg. protein/ml.) was administered intravenously and intraperitoneally to C 57/B16 laboratory mice (0.54 mg./kg. of body weight). In addition, 2 mg. protein/ml of crude extracellular product from *S. intermedius* was administered intraperitoneally weekly for 2 months or or twice a week for 3 weeks. In no instance were mice lost as a result of toxicity.

In view of the apparently low toxicity of the active material, the use thereof in therapy as an immunosuppressive agent appears feasible.

EXAMPLE VII

Inhibition of Jerne Plaque Formation: Primary Humoral Immune Responses

Sheep red blood cells (SRBC) were injected intraperitoneally into six groups of 3-C57B/6 mice on day 0. Each group received 3,000 units (one unit is the amount of material which causes 50% inhibition of PHA-stimulated, fresh human lymphocytes under the condition of the assay) of the material of Example I(b) or phosphate buffered saline (BPS) intraperitoneally. The test groups received the material at days −4, −2, 0, +2, and +4; the control group received PBS at day 0. On day 5, all of the animals were sacrificed and their spleens removed. The spleen cells were dispersed and counted, and duplicate agar plates were poured containing spleen cells, complement and SRBC. Following overnight incubation at 37° C., the number of hemolysis plaques were counted.

| Day Sample Injected | Average number of Plaques/10$^6$ Cells |
|---|---|
| −4 | 575 |
| −2 | 50 |
| 0 | 378 |
| +2 | 3418 |
| +4 | 3472 |
| Control | 2906 |

The results of this study indicate that the bacterial product is capable of inhibiting the Jerne Plaque Assay (antibody production).

EXAMPLE VIII

Alternative Growth Procedures (a) Broth Cultures

Active preparations were obtained by growing *S. intermedius* in static cultures of 2% Tryptone Glucose Broth (TGB) for 48 hours at 37° C., centrifuging the culture after incubation to remove the bacterial cells and concentrating the clarified broth culture by ultrafiltration using an Amicon PM-10 filter.

(b) Plate Cultures

Tryptone Glucose Agar plates were inoculated with *S. intermedius* as in Example I, but without dialysis membranes. The plates, after incubation as in Example I(b) were frozen at −20° C. overnight. The frozen material was removed from the Petri plate and thawed in a cheezecloth-lined funnel. The drippings were collected in a beaker. The agar matrix remained in the cheesecloth, but the fluid of the nutrient material and "bacterial products" were collected. The thus-clarified material in the beaker also has activity by the tests described above.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of producing an extracellular bacterial product having immunosuppressive activity from an oral bacterial organism, comprising the steps of:
   (a) culturing the oral bacterium anaerobically in a culture medium,
   (b) separating the oral bacterium from the culture medium to produce a bacteria-free liquid, and
   (c) fractionating the bacteria-free liquid to remove components having molecular weights less than 10,000 and recovering the remaining fraction of molecular weight in excess of 10,000 as the product having immunosuppressive activity.

2. The method of claim 1 wherein the culture medium is a broth.

3. The method of claim 2 wherein the broth is a Todd-Hewitt Medium.

4. The method of claim 1 wherein said oral bacterial organism is selected from the group consisting of genus Streptococcus and genus Actinomyces.

5. The method of claim 4 wherein the oral bacterial organism is *Streptococcus mutans, Streptococcus intermedius, Streptococcus salivarius, Actinomyces viscosus* or *Actinomyces naeslundii.*

6. The method of claim 4 wherein the oral bacterial organism is
   *Actinomyces naeslundii,*
   *Actinomyces viscosus,*
   *Streptococcus mutans* AHT,
   *Streptococcus mutans* E49,
   *Streptococcus mutans* (ATCC 10449),
   *Streptococcus mutans* BHT,
   *Streptococcus mutans* Fa-1,
   *Streptococcus mutans* IB
   *Streptococcus intermedius,* or
   *Streptococcus salivarius.*

7. The method of claim 1 wherein said oral bacterial organism is *Streptococcus intermedius.*

8. The product of the process of claim 4.

9. The product of the process of claim 5.

10. The product of the process of claim 5 having immunosuppressive activity wherein the organism is *S. mutans* AHT, *S. mutans* BHT, *S. mutans* 10449, *S. mutans* IB, *S. intermedius* or *A. viscosus* and the product inhibits fibroblastoid cells.

11. The product of the process of claim 5, having immunosuppressive activity wherein the organism is *S. mutans* AHT, *S. mutans,* BHT, *S. mutans* Fa-1, *S. mutans* E49, *S. salivarius, S. intermedius, A. viscosus* or *A. naeslundii* and the product inhibits blast transformation of PHA-stimulated human lymphocytes.

12. A proteinaceous extracellular product of *Streptococcus intermedius* having immunosuppressive activity, a molecular weight of about 160,000, as measured by gel filtration, an isoelectric point pI of about 4.8 and an ultraviolet absorption spectrum with a peak absorbance of 280 nm, said agent having inhibitory activity against fibroblastoid cells and against blast transformation of PHA-stimulated human lymphocytes.

13. The method of claim 1 or 3 wherein said culture medium contains substantially no glucose.

14. The method of claim 1 or 3 wherein components having molecular weights less than 50,000 are removed in step (c).

15. The product of claim 14 having immunosuppressive activity and a molecular weight in excess of 50,000.

16. The method of claim 14 wherein said culture medium contains substantially no glucose.

17. The product of claim 16 having immunosuppressive activity and a molecular weight in excess of 50,000.

* * * * *